United States Patent
Liu et al.

(10) Patent No.: US 9,504,653 B2
(45) Date of Patent: Nov. 29, 2016

(54) MICROSPHERE DRUG DELIVERY SYSTEM FOR SUSTAINED INTRAOCULAR RELEASE

(71) Applicant: Allergan, Inc., Irvine, CA (US)

(72) Inventors: Hui Liu, Irvine, CA (US); Jinping Wan, Irvine, CA (US); Patrick M. Hughes, Aliso Viejo, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 14/213,294

(22) Filed: Mar. 14, 2014

(65) Prior Publication Data

US 2014/0294986 A1 Oct. 2, 2014

Related U.S. Application Data

(60) Provisional application No. 61/807,092, filed on Apr. 1, 2013.

(51) Int. Cl.
| | |
|---|---|
| A61K 9/16 | (2006.01) |
| A61K 31/165 | (2006.01) |
| A61K 31/381 | (2006.01) |
| A61K 9/19 | (2006.01) |
| A61K 9/00 | (2006.01) |
| A61F 9/00 | (2006.01) |
| A61K 9/50 | (2006.01) |

(52) U.S. Cl.
CPC .............. *A61K 9/16* (2013.01); *A61F 9/0008* (2013.01); *A61K 9/0048* (2013.01); *A61K 9/19* (2013.01); *A61K 9/5089* (2013.01); *A61K 31/165* (2013.01); *A61K 31/381* (2013.01)

(58) Field of Classification Search
None
See application file for complete search history.

(56) References Cited

U.S. PATENT DOCUMENTS

| | | | |
|---|---|---|---|
| 4,798,823 A | 1/1989 | Witzel | |
| 5,214,130 A | 5/1993 | Patchett et al. | |
| 5,688,819 A | 11/1997 | Woodward et al. | |
| 5,741,810 A | 4/1998 | Burk | |
| 5,834,498 A | 11/1998 | Burk | |
| 6,124,344 A | 9/2000 | Burk | |
| 6,294,563 B1 | 9/2001 | Garst | |
| 6,309,669 B1 | 10/2001 | Setterstrom et al. | |
| 6,395,787 B1 | 5/2002 | Woodward et al. | |
| 6,403,649 B1 | 6/2002 | Woodward et al. | |
| 6,602,900 B2 | 8/2003 | Burk | |
| 7,589,057 B2 | 9/2009 | Chang et al. | |
| 7,799,336 B2 | 9/2010 | Hughes | |
| 7,828,996 B1 | 11/2010 | Davalian | |
| 7,993,634 B2 | 8/2011 | Hughes et al. | |
| 8,034,366 B2* | 10/2011 | Shiah et al. | 424/426 |
| 8,206,736 B2 | 6/2012 | Hughes | |
| 8,206,737 B2 | 6/2012 | Hughes | |
| 8,445,027 B2 | 5/2013 | Hughes et al. | |
| 2002/0198249 A1 | 12/2002 | Burk | |
| 2003/0186855 A1 | 10/2003 | Or et al. | |
| 2003/0212249 A1 | 11/2003 | Naicker et al. | |
| 2005/0244464 A1 | 11/2005 | Hughes | |
| 2006/0173060 A1 | 8/2006 | Chang et al. | |
| 2006/0182781 A1 | 8/2006 | Hughes et al. | |
| 2006/0246145 A1 | 11/2006 | Chang et al. | |
| 2007/0099984 A1 | 5/2007 | Burk | |
| 2007/0212395 A1 | 9/2007 | Donello et al. | |
| 2007/0224246 A1 | 9/2007 | Hughes | |
| 2007/0293873 A1 | 12/2007 | Chang | |
| 2008/0033351 A1 | 2/2008 | Trogden et al. | |
| 2008/0107694 A1* | 5/2008 | Trogden et al. | 424/400 |
| 2008/0131481 A1 | 6/2008 | Hughes | |
| 2008/0131482 A1 | 6/2008 | Hughes | |
| 2009/0148527 A1* | 6/2009 | Robinson et al. | 424/484 |
| 2009/0264813 A1 | 10/2009 | Chang | |
| 2010/0104654 A1 | 4/2010 | Robinson et al. | |
| 2010/0204325 A1 | 8/2010 | Blanda et al. | |
| 2010/0247606 A1 | 9/2010 | Robinson et al. | |
| 2010/0278898 A1 | 11/2010 | Hughes et al. | |
| 2011/0118825 A1 | 5/2011 | Hunter et al. | |
| 2011/0182966 A1 | 7/2011 | Robinson et al. | |
| 2011/0250285 A1 | 10/2011 | Hughes et al. | |
| 2012/0219611 A1 | 8/2012 | Hughes | |
| 2012/0238633 A1 | 9/2012 | Hughes | |
| 2013/0017268 A1 | 1/2013 | Robinson et al. | |

FOREIGN PATENT DOCUMENTS

| | | |
|---|---|---|
| WO | 03024420 A1 | 3/2003 |
| WO | 2005110424 A1 | 11/2005 |
| WO | 2008070402 A2 | 6/2008 |
| WO | 2009142388 A2 | 11/2009 |
| WO | 2010062523 A2 | 6/2010 |
| WO | 2010111449 A1 | 9/2010 |

OTHER PUBLICATIONS

Nichols, Michael (Factors Affecting Size and Swelling of Poly(ethylene glycol) Hydrogel Microspheres Formed in Aqueous Sodium Sulfate Solutions; Master of Science Dissertation, Jan. 2009).*
Resomer® Biodegradable Polymers for Medical Device Applications Research product page (retrieved from <http://www.sigmaaldrich.com/materials-science/polymer-science/resomer.html> on 77/22/2016).*
Resomer RG 753 S Technical Information page (retrieved from <http://www.resomer.com/sites/lists/HN/ProductSpecifications/TI-RESOMER-RG-753-S-EN.pdf> on Jul. 22, 2016).*
Tejpal et al. (Journal of Drug Delivery & Therapeutics; 2013, 3(1), 114-123).*

(Continued)

*Primary Examiner* — Patricia Duffy
*Assistant Examiner* — Garen Gotfredson
(74) *Attorney, Agent, or Firm* — Joel German (57) ABSTRACT

Disclosed are biodegradable microspheres between 40 μm and 200 μm in diameter that are effectively retained in the anterior chamber of the eye without producing hyperemia. The microspheres generally contain a drug effective for the treatment of an ocular condition and include a biodegradable polymer matrix that can provide for the sustained (>7 day) release of the drug following administration to the anterior chamber of the eye. Methods for making and using the microspheres to treat an ocular condition are also disclosed.

17 Claims, 5 Drawing Sheets

(56) References Cited

OTHER PUBLICATIONS

U.S. Appl. No. 61/297,660, filed Jan. 22, 2010.
U.S. Appl. No. 10/837,260, filed Apr. 30, 2004.
U.S. Appl. No. 11/303,462, filed Dec. 15, 2005.
U.S. Appl. No. 11/368,845, filed Mar. 6, 2006.
U.S. Appl. No. 11/371,118, filed Mar. 8, 2006.
U.S. Appl. No. 11/395,019, filed Mar. 31, 2006.
U.S. Appl. No. 12/028,762, filed Feb. 8, 2008.
U.S. Appl. No. 12/028,763, filed Feb. 8, 2008.
U.S. Appl. No. 12/411,250, filed Mar. 25, 2009.
U.S. Appl. No. 12/761,765, filed Apr. 16, 2010.
U.S. Appl. No. 13/011,467, filed Jan. 21, 2011.
U.S. Appl. No. 13/152,780, filed Jun. 3, 2011.
U.S. Appl. No. 13/466,752, filed May 8, 2012.
U.S. Appl. No. 13/466,804, filed May 8, 2012.
Bron et al. (2007) "Methodologies to Diagnose and Monitor Dry Eye Disease:Report of the Diagnostic Methodology Subcommittee of the International Dry Eye WorkShop (2007)" Ocul. Surf. 5(2):108-152.
Chemical Abstracts Service (CAS) No. 155206-00-1 [online], 3 pages, [retrieved on Mar. 29, 2013], American Chemical Society (ACS), retrieved from SciFinder® URL: www.cas.org.
Chemical Abstracts Service (CAS) No. 215863-14-2 [online], 2 pages, [retrieved on Mar. 29, 2013], American Chemical Society (ACS), retrieved from SciFinder® URL: www.cas.org.
Doucet et al. (1998) "O/W emulsion and W/O/W multiple emulsion:physical characterization and skin pharmacokinetic comparison in the delivery process of caffeine" International Journal of Cosmetic Science 20, 283-295.
Eberle et al. (1992) "Synthesis of the Main Metabolite (OL-17) of Cyclosporin A" J. Org. Chem., 57, 2689-2691.
Evonik Industries, Standard polymers product listing [online], 3 pages, [retrieved on Mar. 29, 2013], retrieved from Evonik Industries website at URL: http://biomaterials.evonik.com/product/biomaterials/en/products-and-services/products/standard-polymers/Pages/default.aspx.
Handbook of Pharmaceutical Salts, P.Heinrich Stahal& Camille G. Wermuth (Eds), Verlag Helvetica Chemica Acta-Zürich, 2002, 329-345).
Higginbotham et al. (2002) "One-Year, Randomized Study Comparing Bimatoprost and Timolol in Glaucoma and Ocular Hypertension" Archives of Ophthalmology vol. 120(10): 1286-1293.
International Search Report for PCT/US2010/028584, mailed Aug. 3, 2010.
Jain, Rajeev A. (2000) "The manufacturing techniques of various drug loaded biodegradable poly(lactide-co-glycolide) (PLGA) devices" Biomaterials 21:2475-2490.
Jain et al. (1998) "Controlled Drug Delivery by Biodegradable Poly(Ester) Devices: Different Preparative Approaches" Drug Development and Industrial Pharmacy, 24(8), 703-727.
Janoria et al. (2007) "Novel approaches to retinal drug delivery" Expert opinion on drug delivery 4:371-388.
Kumar et al, "Novel approaches to retinal drug delivery", Expert Opinion on Drug Delivery, Informa Healthcare, GB LNKD-DOI: 10, 1517/17425247.4.4.371, vol. 4, Jul. 1, 2007, pp. 371-388, XP009131521 ISSN: 1742-5247.
Lemp et al. (2007) "The Definition and Classification of Dry Eye Disease: Report of the Definition and Classification Subcommittee of the International Dry Eye Workshop" Ocul. Surf. 5:75-92.
Marquis et al. (2005) "Management of glaucoma: focus on pharmacological therapy" Drugs and Aging 22(1):1-21.
Müther, Philipp Sebastian (May 24, 2006) "Development of a Resorbable Anterior Chamber Glaucoma Implant" Dissertation, Rheinland-Westfalen Technical College, Aachen, German language, 98 pages.
Hubler et al. (2000) "Synthetic Routes to NEt Xaa4-Cyclosporin A Derivatives as Potential Anti-HIV I Drugs" Tet. Lett., 41, 7193-7196.
Pflugfelder et al. (2004) "Antiinflammatory Therapy of Dry Eye", Am. J. Ophthalmol. 137:337-342.
Weiner (Mar. 2011) "What is a Continuous Particle Size Distribution" Brookhaven Instruments Corporation White Paper (www.brookhaveninstruments.com), pp. 1-3.
Weiner (May 2011) "What is a Discrete Particle Size Distribution" Brookhaven Instruments Corporation White Paper (www.brookhaveninstruments.com), pp. 1-4.
Woodward et al. (2007) "Fixed-combination and emerging glaucoma therapies" Expert Opin Emerg Drugs 12 (2):313-27.
Woodward et al. (2007) "Identification of an antagonist that selectively blocks the activity of prostamides (prostaglandinethanolamides) in the feline iris" British Journal of Pharmamlogy 150:342-352.
Woodward et al, "Prostamides (prostaglandin-ethanolamides) and their pharmacology", British Journal of Pharmacology (2008), 153, pp. 410-419.
Herrero-Vanrell, Rocio et al, Biodegradable Microspheres for Vitreoretinal Drug Delivery, Advanced Drug Delivery Reviews 52, 2001, pp. 5-16.

* cited by examiner

140um placebo PLA macrospheres in monkey's IC area

FIG. 3

Baseline

Day 1

Day 2

Day 4

Severe and lasting hyperemia when 10 µl of a PLGA microsphere placebo suspension with mean size of 35 µm was injected into dog intracamerally.

FIG. 4

Macrospheres in the angle of a dog

FIG. 5

Top view of macrosphere settle into monkey anterior angle

FIG. 6

Side view of two monkey eyes. The injection eye (left) shows a macrosphere mass fits into anterior angle with minimal contact to corneal; the control eye (right) indicates the empty space.

FIG. 7

MICROSPHERE DRUG DELIVERY SYSTEM FOR SUSTAINED INTRAOCULAR RELEASE

CROSS-REFERENCE

This application claims priority under 35 U.S.C. §119 (e) from U.S. Provisional Application Ser. No. 61/807,092, filed Apr. 1, 2013, which is hereby incorporated by reference in its entirety.

BACKGROUND

The present invention relates to a biodegradable drug delivery system comprising a plurality of microspheres between 40 µm and 200 µm in diameter that are effectively retained in the anterior chamber of the eye for an extended period (such as for about 1-12 months) without producing hyperemia. The microspheres generally contain a drug effective for the treatment of an ocular condition and a biodegradable polymer matrix that provides for continuous and sustained (>7 day) release of the drug following administration to the anterior chamber of the eye. The drug may be encapsulated and/or dispersed within the biodegradable polymer matrix. Pharmaceutical compositions comprising these microspheres, methods for making these microspheres, and methods of administering the microspheres to the anterior chamber (or optionally the vitreous body) of the eye to treat an ocular condition such as glaucoma, elevated intraocular pressure, and inflammation, are also described.

While microspheres and extruded implants have been used in the past for the localized delivery of a drug into the anterior or posterior segment of the eye, conventional microspheres and extruded implants suffer from certain drawbacks. Conventional microspheres used in ocular methods commonly have particle sizes ranging from about 1-30 µm. However, we have discovered that microspheres of this size are poorly tolerated inside the eye due to significant inflammation, which may be due to phagocytosis of the microspheres inside the eye. As a result severe hyperemia may occur when microspheres of this size are injected into an ocular region of the eye such as the anterior chamber or subTenon's space. Additionally, microspheres that are less than about 30 or 40 µm in diameter are not effectively retained in the anterior chamber after intracameral administration. While not wishing to be bound by any theory, it is believed that microspheres with diameters less than about 30 µm are quickly cleared from the anterior chamber through the trabecular meshwork, a 3 dimensional sponge-like structure with pore sizes ranging from 20-30 µm.

Extruded implants have also been investigated for administration to the anterior chamber of the eye. However, the implants must be very small to fit through a small gauge needle (25 gauge or smaller). The implants must also be small enough to fit into the angle formed by the cornea and iris without touching the corneal endothelium. This limits the size of the implant and greatly reduces the potential drug load. These size limitations restrict the use of implants to only very potent compounds. Additionally, it is technically very challenging to manufacture, weigh, cut, and load these implants into an injectable device.

An additional disadvantage of a typical PLGA extruded implant used for this route of administration is swelling. An implant may swell to 2-3 times its original size after being injected into the anterior chamber. Swollen implants may damage corneal endothelium cells, severely limiting the population of patients suitable for this treatment.

Accordingly, the present disclosure describes a biodegradable "microsphere" drug delivery system that can be used for intracameral administration of a drug with little if any of the side effects described above. The system comprises a plurality of biodegradable, drug-containing, spherical (or substantially spherical) particles (microspheres) with diameters (and therefore particles sizes) ranging from 40 to 200 µm, with a mean diameter between 60 and 150 µm. In one embodiment the microspheres in the drug delivery system have diameters of between about 100 µm and about 180 µm with a mean diameter of between about 100 and about 150 µm.

The particle size requirement ensures that phagocytosis of the particles within the eye is minimized or eliminated altogether and prevents immediate clearance of the particles across the trabecular meshwork. Nevertheless, despite their size, the microspheres can be easily injected into the anterior chamber or other ocular region in the eye using small gauge needles (25 gauge and smaller). Furthermore, a much higher dose can be given since the diameter and length limitations of rod shaped implants are overcome. Doses up to a few milligrams of drug can be administrated via 20 µL injections. In comparison, most extruded implant system active dosages are less than 1 mg. The microspheres do not swell as much as typical implants as they hydrate, hence more total polymer can be administered. Microspheres also allow for easy dose adjustment, and can be readily manufactured in gram to kilogram quantities using aseptic processing techniques. Moreover, with a suitable polymer or polymer combination, the microspheres can provide for the sustained release of a therapeutic agent directly into the anterior chamber of the eye to more effectively treat an ocular condition of the anterior segment of the eye without the need for daily administration of the agent, which may or may not effectively reach the affected region of the eye in an effective manner.

SUMMARY

The present invention provides a drug delivery system effective for the sustained and localized delivery of a therapeutic agent into the anterior chamber of the eye without causing hyperemia (eye redness) or painful inflammation.

The drug delivery system may be effective for the treatment of an ocular condition and comprises or consists of a plurality of biodegradable microspheres and an ophthalmically acceptable carrier. The biodegradable microspheres comprise or consist of a biodegradable polymer matrix and a therapeutic agent effective for the treatment of the ocular condition. The therapeutic agent may be dispersed within and/or encapsulated by the polymer matrix. The therapeutic agent-containing microspheres can be produced by an emulsion process, such as, for example, an oil-in-water emulsion process, that includes steps for selecting for microspheres of particular sizes.

To satisfy the requirements of the drug delivery system, the microspheres present in the delivery system should have diameters (and therefore particle sizes) greater than 40 µm but less than 200 µm. In one form of the invention, the microspheres injected into the intracameral space (anterior chamber) of an eye are no less than 100 µm and no larger than 150 µm in diameter. In another form, the diameters of the microspheres injected into the intracameral space of an eye are no less than about 106 µm and no larger than about 180 µm. Microspheres larger than 200 µm may tend to settle quickly and can be more difficult to inject with small gauge needles than smaller spheres. Additionally, microsphere populations with particle sizes exceeding 200 µm may irritate endothelial cells in the eye.

In some forms of the present invention, the population of microspheres present in a drug delivery system may be defined in terms of the mean diameter (or mean particle size) and polydispersity (particle size distribution) of the population, though other measures of central tendency may be used such as modal and median diameter, where the modal diameter is the diameter that occurs most often in a population of microspheres, and the median diameter is the diameter below which lies 50% of the microspheres. The mean diameter is the average diameter.

Measures of polydispersity include the full width at half maximum (FWHM), d90/d10, d75/d25, and d90–d10 (the span). The FWHM is obtained from the differential size distribution of particles by drawing a horizontal line at 50% of the maximum and taking the difference between the two intersection points in the distribution curve. Other measures that may be derived from the differential size distribution include the mean and modal diameter. The d90 and d10 are the diameters below which 90% and 10% of the particles fall. The value d50 is the median diameter, or diameter below which 50% of the particles fall, and d75 and d25 are the diameters below which 75% and 25% of the particles fall, respectively.

The size and polydispersity of a microsphere population can be measured using laser light scattering methods. Instruments suitable for measuring the size and polydispersity of a microsphere population are commercially available, from, for example, Malvern Instruments Ltd. Microspheres containing a therapeutic agent, such as those produced by emulsion methods, may be spherical or substantially spherical. In these instances, the particle size(s) measured and reported by such instruments for a sample of microspheres will essentially represent the diameter(s) of the microspheres.

Accordingly, in one embodiment of the present invention, the mean diameter (or particle size) of the microspheres present in the drug delivery system is between 40 and 200 µm, between 60 and 140 µm, between 100 and 150 µm, or between 110 and 150 µm. In a specific embodiment the mean diameter of the microspheres is about 136 µm, about 140 µm, about 147 µm, or about 150 µm. In each of these embodiments, the drug delivery system comprises no microspheres less than 40 µm in diameter and no microspheres greater than 200 µm in diameter. In particular embodiments the microspheres present in the drug delivery system have a unimodal particle size distribution and the diameters of the microspheres present in the drug delivery system deviate from the mean diameter by no more than about 10, 20, 30, 40, 50, or 60 µm.

Thus, some embodiments of the invention provide for a drug delivery system, comprising a plurality of biodegradable microspheres and an ophthalmically acceptable carrier, the microspheres comprising a biodegradable polymer matrix and a therapeutic agent effective for the treatment of an ocular condition, wherein the microspheres present in the drug delivery system have diameters no less than 40 µm and no greater than 200 µm. More specifically, the microspheres present in the drug delivery system may have diameters no less than 60 µm and no greater than 150 µm. For example, the microspheres present in the drug delivery system may have diameters no less than about 100 µm and no greater than about 180 µm. In another variation, the microspheres present in the drug delivery system have diameters no less than 100 µm and no greater than 150 µm.

In another embodiment, the modal diameter of the microspheres present in the drug delivery system is between 40 and 200 µm, between 60 and 140 µm, or between 130 and 140 µm. In a specific embodiment the modal diameter of the microspheres is about 136 µm, about 140 µm, about 147 µm, or about 150 µm.

In another embodiment, median diameter of the microspheres present in the drug delivery system is between 40 and 200 µm, between 60 and 140 µm, or between 130 and 140 µm. In a specific embodiment the median diameter of the microspheres is about 136 µm, about 140 µm, about 147 µm, or about 150 µm.

In some embodiments of the present invention, the microspheres present in the drug delivery system may have a unimodal particle size distribution.

In some embodiments, the span (d90–d10) of the microspheres in the drug delivery system may be no more than about 5, 10, 20, 30, 40, 50, or 60 µm. In some forms, the polydispersity of the microspheres in the drug delivery system, as measured by the percentile ratio d90/d10, is not more than about 5, 4, 3, 2, or 1.5. In other forms, the polydispersity of the microspheres in the drug delivery system, as measured by the FWHM, is not more than about 10, 20, 30, 40, 50, or 60 µm.

In particular embodiments the microspheres present in the drug delivery system have a unimodal particle size distribution and the diameters of the microspheres present in the drug delivery system deviate from the mean diameter by no more than about 10, 20, 30, 40, 50, or about 60 µm.

In another embodiment the microspheres present in the drug delivery system have a unimodal particle size distribution and the diameters the microspheres present in the drug delivery system deviate from the modal diameter by no more than about 10, 20, 30, 40, 50, or about 60 µm.

In a useful embodiment the microspheres in the drug delivery system have diameters no less than 40 µm and no more than 200 µm with a mean diameter between 100 µm and 150 µm.

In another useful embodiment the microspheres in the drug delivery system have diameters no less than about 60 µm and no more than 200 µm. Accordingly, the drug delivery system comprises no microspheres less than about 60 µm or more than 200 µm in diameter.

In some embodiments the microspheres in the drug delivery system have diameters no less than about 100 µm and no more than about 180 µm.

In a specific embodiment the microspheres in the drug delivery system have diameters no less than about 106 µm and no more than about 180 µm.

In some embodiments the microspheres in the drug delivery system have diameters no less than about 130 µm and no more than about 150 µm.

Some embodiments relate to a method of using a drug delivery system according to the present invention to treat an ocular condition, including for example, an anterior ocular condition, in a patient, the method comprising placing the drug delivery system in the eye(s) affected by the ocular condition. An anterior ocular condition is a disease or condition which affects or which involves an anterior (front of the eye) ocular region or site, such as a periocular muscle, eye lid, or an eye tissue, fluid, or structure located anterior to the posterior wall of the lens capsule or ciliary muscles. Thus, an anterior ocular condition primarily affects or involves the conjunctiva, the cornea, the anterior chamber, the aqueous humor, the iris, the ciliary body, the lens or the lens capsule and blood vessels and nerves which vascularize or innervate an anterior ocular region or site.

Accordingly, examples of an ocular condition that may potentially be treated with the presently described drug delivery systems include, but are not limited to, an inflammation of the eye, including, for example, an inflammation in or of the anterior segment of the eye; aphakia; pseudophakia; rubeosis iridis; neovascularization in the eye, including for example neovascularization of the iris or cornea; astigmatism; blepharospasm; infections, such as viral or fungal infections; conjunctivitis; corneal diseases; corneal ulcer; dry eye syndrome (keratoconjunctivitis sicca); eyelid diseases; lacrimal apparatus diseases; lacrimal duct obstruction; myopia; presbyopia; pupil disorders; strabismus; elevated intraocular pressure (also referred to as ocular hypertension); and glaucoma. Glaucoma can be considered to be an anterior ocular condition because a clinical goal of glaucoma treatment can be to reduce a hypertension of aqueous fluid in the anterior chamber of the eye (that is, to reduce intraocular pressure). Glaucoma is a disease of the eye characterized by increased (elevated) intraocular pressure.

Thus, one embodiment is a method for treating an ocular condition in a patient in need thereof, comprising placing (e.g., injecting) a drug delivery system according to the present invention into the anterior chamber of an eye of the patient, thereby reducing or relieving at least one sign or symptom of the ocular condition. Suitable injection volumes for these methods may vary from about 10 μL (microliters) to about 50 μL. Injection volumes of 10 μL or 20 μL are well tolerated and acceptable.

The patient in whose eye the microspheres have been placed receives a therapeutically effective amount of a therapeutic agent effective for treating the ocular condition for an extended period without requiring additional administrations of the agent or agents. For example, in some embodiments, the patient receives a therapeutically effective amount of a therapeutic agent for at least about one week, at least about one month, at least about two months, at least about 3 months, or at least about 6 months after placement of the drug delivery system in the anterior chamber. Such extended release times may facilitate successful treatment results, rapid recovery from the condition, and eliminate the need for repeated daily application of the drug.

The ability to deliver therapeutically effective levels of a drug directly into the anterior chamber for extended periods without causing hyperemia or inflammation makes it possible to more effectively treat ocular conditions affecting and associated with the tissues and structures in the anterior segment of the eye, including the lens, the corneal endothelium, the iris-ciliary body, Schlemm's canal, and the trabecular meshwork. Importantly, placement of a sustained-release drug delivery system in the anterior chamber of the eye provides for an effective means of treating elevated intraocular pressure (ocular hypertension), which may be due to decreased clearance of aqueous humor through the trabecular meshwork. Accordingly, microspheres in accordance with the present disclosure comprise a therapeutic agent effective for the treatment of an ocular condition (such as, for example, glaucoma or, more generally, elevated intraocular pressure) and a biodegradable polymer matrix associated with and/or encapsulating the therapeutic agent. The microspheres may be placed in the anterior chamber of the eye to thereby treat the ocular condition for an extended period (e.g., for 1-6 months).

A drug delivery system and/or microspheres according to the present invention may optionally further comprise one or more pharmaceutically acceptable excipients, such as one or more buffering agents, tonicity agents, preservatives, or polyethylene glycols.

Suitable buffering agents include, without limitation, alkali and alkaline earth carbonates, phosphates, bicarbonates, citrates, borates, acetates, succinates and the like, such as sodium phosphate, citrate, borate, acetate, bicarbonate, carbonate and the like. These agents are advantageously present in amounts sufficient to maintain a pH of the system of between 2 and 9 and more preferably between about 4 and about 8.

Suitable preservatives include sodium bisulfite, sodium bisulfate, sodium thiosulfate, ascorbate, benzalkonium chloride, chlorobutanol, thimerosal, phenylmercuric acetate, phenylmercuric borate, phenylmercuric nitrate, parabens, methylparaben, polyvinyl alcohol, benzyl alcohol, phenylethanol and the like and mixtures thereof.

Useful tonicity agents include glycerin, sugar alcohols, xylitol, sorbitol, glycerol, erythritol, mannitol, salts, potassium chloride and/or sodium chloride.

Useful polyethylene glycols have a molecular weight of about 300 to about 40,000. Specific examples of polyethylene glycols that may be included in a microsphere formulation include polyethylene glycol 3350 (PEG 3350), PEG 4400, and PEG 8000. In other instances, a polyethylene glycol with a molecular weight of about 20,000 (PEG 20K) may be used.

In accordance with the present invention, the therapeutic agent contained by the microspheres and therefore present in the drug delivery system, is one that is effective for the treatment of the ocular condition. In particular embodiments, the therapeutic agent and therefore the drug delivery system is effective for the treatment of elevated intraocular pressure (ocular hypertension), glaucoma, and inflammation in an eye in a patient. In one embodiment the therapeutic agent is effective for reducing, and thereby relieving, ocular hypertension or inflammation in the eye.

Useful therapeutic agents may include, without limitation, prostaglandins, prostaglandin prodrugs, proteins, peptides (polypeptides having a molecular mass less than 2 kDa), prostamides, cyclosporine A, beta blockers, alpha agonists, carbonic anhydrase inhibitors Rho Kinase inhibitors, squalamine, antiparasitics, antifungals, antihistamines, antibiotics, tyrosine kinase inhibitors, alpha 2 adrenergic receptor agonists, immunosuppressive agents, beta blockers, anti muscarinic agents, steroidal anti-inflammatory agents, non-steroidal anti-inflammatory agents, antineoplastic agents, antiviral agents, antioxidants, and other therapeutic agents as may be listed above and below. The therapeutic agent used may be in a free base or free acid form, depending on the chemical formula of the agent, or may be in the form of a pharmaceutically acceptable salt.

Pharmaceutically acceptable salts are salts or complexes that retain the desired biological activity of the compound and exhibit minimal or no undesired toxicological effects to the patient to which they are administered.

Prostamides have been described by, for example, Woodward et al. (2007) British Journal of Pharmacology 150: 342-352. Useful prostamides for reducing ocular hypertension or elevated intraocular pressure may include those disclosed in, for example, U.S. Pat. Nos. 5,834,498, 7,799,336, and in U.S. Patent Application Publication 2002/0198249. One example of a useful prostamide is bimatoprost (CAS No. 155206-00-1). Another example of a useful prostamide is the compound represented by CAS No. 215863-14-2 and having the formula:

In some embodiments, the microspheres may comprise a prostamide having the formula (I):

or a pharmaceutically acceptable salt thereof, wherein the dashed bonds represent a single or double bond which can be in the cis or trans configuration, A is an alkylene or alkenylene radical having from two to six carbon atoms, which radical may be interrupted by one or more oxide radicals and substituted with one or more hydroxy, oxo, alkyloxy or alkylcarboxy groups wherein said alkyl radical comprises from one to six carbon atoms; B is a cycloalkyl radical having from three to seven carbon atoms, or an aryl radical, selected from the group consisting of hydrocarbyl aryl and heteroaryl radicals having from four to ten carbon atoms wherein the heteroatom is selected from the group consisting of nitrogen, oxygen and sulfur atoms; X is $-N(R^4)_2$ wherein $R^4$ is independently selected from the group consisting of hydrogen and a lower alkyl radical having from one to six carbon atoms; Z is $=O$ or represents 2 hydrogen radicals; one of $R^1$ and $R^2$ is $=O$, $-OH$ or a $-O(CO)R^6$ group, and the other one is $-OH$ or $-O(CO)R^6$, or $R^1$ is $=O$ and $R^2$ is H, wherein $R^6$ is a saturated or unsaturated acyclic hydrocarbon group having from 1 to about 20 carbon atoms, or $-(CH_2)_m R^7$ wherein m is 0 or an integer of from 1 to 10, and $R^7$ is cycloalkyl radical, having from three to seven carbon atoms, or a hydrocarbyl aryl or heteroaryl radical, as defined above.

Useful prostaglandin prodrugs include, without limitation, latanoprost and travoprost.

Useful steroidal anti-inflammatory agents include corticosteroids, 21-acetoxypregnenolone, alclometasone, algestone, amcinonide, beclomethasone, beclomethasone dipropionate, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

Useful non-steroidal anti-inflammatory agents include ketorolac, aspirin, diclofenac, flurbiprofen, ibuprofen, naproxen, suprofen, and combinations thereof.

Useful proteins include antibodies, DARPins (designed ankyrin repeat proteins), and anticalins. Specific examples include anti-VEGF antibodies, anti-VEGF DARPins, and anti-VEGF anticalins, any of which may be useful for inhibiting and reducing neovascularization in the eye, and thereby for treating an ocular condition associated with neovascularization in the eye.

Useful antihistamines include, and are not limited to, loradatine, hydroxyzine, diphenhydramine, chlorpheniramine, brompheniramine, cyproheptadine, terfenadine, clemastine, triprolidine, carbinoxamine, diphenylpyraline, phenindamine, azatadine, tripelennamine, dexchlorpheniramine, dexbrompheniramine, methdilazine, and trimprazine doxylamine, pheniramine, pyrilamine, chiorcyclizine, thonzylamine, and derivatives thereof.

Useful antibiotics include without limitation, cefazolin, cephradine, cefaclor, cefapirin, ceftizoxime, cefoperazone, cefotetan, cefutoxime, cefotaxime, cefadroxil, ceftazidime, cephalexin, cephalothin, cefamandole, cefoxitin, cefonicid, ceforanide, ceftriaxone, cefadroxil, cephradine, cefuroxime, ampicillin, amoxicillin, cyclacillin, ampicillin, penicillin G, penicillin V potassium, piperacillin, oxacillin, bacampicillin, cloxacillin, ticarcillin, azlocillin, carbenicillin, methicillin, nafcillin, erythromycin, tetracycline, doxycycline, minocycline, aztreonam, chloramphenicol, ciprofloxacin hydrochloride, clindamycin, metronidazole, gentamicin, lincomycin, tobramycin, vancomycin, polymyxin B sulfate, colistimethate, colistin, azithromycin, augmentin, sulfamethoxazole, trimethoprim, and derivatives thereof.

Useful beta blockers include acebutolol, atenolol, labetalol, metoprolol, propranolol, timolol, and derivatives thereof.

Useful antineoplastic agents include adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, taxol and derivatives thereof, taxotere and derivatives thereof, vinblastine, vincristine, tamoxifen, etoposide, piposulfan, cyclophosphamide, and flutamide, and derivatives thereof.

Useful immunosuppressive agents include cyclosporine, azathioprine, tacrolimus, and analogs thereof.

Useful antiviral agents include interferon gamma, zidovudine, amantadine hydrochloride, ribavirin, acyclovir, valciclovir, dideoxycytidine, phosphonoformic acid, ganciclovir, and derivatives thereof.

Useful antioxidant agents include ascorbate, alpha-tocopherol, mannitol, reduced glutathione, various carotenoids, cysteine, uric acid, taurine, tyrosine, superoxide dismutase, lutein, zeaxanthin, cryotpxanthin, astazanthin, lycopene, N-acetyl-cysteine, carnosine, gamma-glutamylcysteine, quercitin, lactoferrin, dihydrolipoic acid, citrate, *Ginkgo Biloba* extract, tea catechins, bilberry extract, vitamins E or esters of vitamin E, retinyl palmitate, and derivatives thereof.

Useful alpha 2 adrenergic receptor agonists include brimonidine (free base or tartrate salt).

Ocular conditions which may benefit from treatment with an anti-inflammatory agent, such as a steroidal anti-inflammatory agent or non-steroidal anti-inflammatory agent, include inflammation in the eye and inflammation-mediated conditions in the eye, including pain. The inflammation may be an inflammation of the front of the eye or anterior segment of the eye.

Ocular conditions which may benefit from the treatment with a tyrosine kinase inhibitor include, but are not limited to, neovascularization (the abnormal formation of new blood vessels), including corneal and iris neovascularization.

Patients that may benefit from treatment with a prostamide or prostaglandin include those suffering from elevated intraocular pressure (ocular hypertension) and, more specifically, glaucoma. Advantageously, the present microspheres are effective in relieving a hypertensive eye by reducing the intraocular pressure in the eye for extended periods (for example, 3 or even 6 months or more) while causing little or no ocular hyperemia (eye redness). For example, one embodiment of the invention provides for a method of reducing elevated intraocular pressure in a patient, comprising injecting a drug delivery system according to the present invention into the anterior chamber of an eye in the patient, thereby reducing intraocular pressure in the eye for one, two, three, or six months or more. In one form of this method the microspheres present in the drug delivery system comprise a prostamide or prostaglandin and have diameters of between 40 μm and 200 μm.

Another embodiment of the present invention provides for a method of making microspheres using an oil-in-water emulsion process, the process comprising
  a) dissolving a biodegradable polymer or combination of biodegradable polymers and a quantity of therapeutic agent in an organic solvent or mixture of organic solvents to form a solution;
  b) adding a saturating or non-saturating quantity of therapeutic agent to an aqueous solution of polyvinyl alcohol to form a second solution;
  c) adding the first solution to the second solution dropwise under constant stirring to form an emulsion;
  d) evaporating the organic solvent(s) under constant stirring to form a suspension;
  e) filtering the suspension through first and second sieves, wherein the mesh size of the first sieve is larger than the mesh size of the second sieve;
  f) collecting particles with diameters smaller than the mesh size of the first sieve and larger than the mesh size of the second sieve;
  g) centrifuging the collected particles to obtain a pellet;
  h) lyophilizing the pellet to form a microsphere preparation.

Step g can comprise two wash steps, wherein the pellet is washed twice with water (such as ultra pure water) to remove residual surfactant and polymer debris. In some forms of this method the stirring rate in Step c is about 10 to about 60 rpm. In other forms the stirring rate is about 300 rpm.

The mean particle size and polydispersity of a microsphere preparation can be determined by laser diffraction using any appropriate instrument. One example is a Malvern Mastersizer 2000 (Malvern Instrument, UK).

In some embodiments the microspheres may include two or more therapeutic agents that may each be effective in treating an ocular condition. In other embodiments, the microspheres comprise a single therapeutic agent.

The microspheres may comprise from about 5% to about 50% by weight of a therapeutic agent. In some embodiments the microspheres comprise from about 5% to about 30% by weight of a therapeutic agent. When more than one therapeutic agent is included, their combined weights constitute the total weight of therapeutic agent.

As described previously, the microspheres may comprise or consist of a biodegradable polymer matrix, a therapeutic agent effective for the treatment of an ocular condition, and optionally a pharmaceutically acceptable excipient. The biodegradable polymer matrix can comprise or consist of a poly(D,L-lactide), a poly(D,L-lactide-co-glycolide), a poly (ortho ester), a poly(phosphazine), a poly(phosphate ester), a polycaprolactone, a polyethylene glycol, a naturally occurring polymer, or any combination thereof. Useful naturally occurring polymers include gelatin and collagen. Some microspheres may comprise both a poly(D,L-lactide) and a poly(D,L-lactide-co-glycolide).

Other polymers of interest include without limitation polyvinyl alcohol, polyanhydrides, polyamines, polyesteramides, polydioxanones, polyacetals, polyketals, polycarbonates, polyphosphesters, polyethers, polyesters, polybutylene, terephthalate, polyorthocarbonates, polyphosphazenes, succinates, poly(malic acid), poly(amino acids), polyvinypyrrolidone, polysaccharides, copolymers, terpolymers, and combinations thereof that are biocompatible and may be biodegradable.

Suitable biodegradable polymers for use in the microspheres include those which are biocompatible, with the eye so as to cause no substantial interference with the functioning or physiology of the eye. Such materials preferably are at least partially and more preferably substantially completely biodegradable or bioerodible. Additional preferred characteristics of the polymers include compatibility with the therapeutic agent, ease of use of the polymer in making the drug delivery systems of the present invention, a half-life in the physiological environment of at least about 6 hours, preferably greater than about one day, not significantly increasing the viscosity of the vitreous, and water insolubility.

The biodegradable polymeric materials which are included to form the matrix are desirably subject to enzymatic or hydrolytic instability. Water soluble polymers may be cross-linked with hydrolytic or biodegradable unstable cross-links to provide useful water insoluble polymers. The degree of stability can be varied widely, depending upon the choice of monomer, whether a homopolymer or copolymer is employed, employing mixtures of polymers, and whether the polymer includes terminal acid groups.

Polylactide, or PLA, includes poly (D-lactide), poly (L-lactide), and poly (D,L-lactide), and may also be identified by CAS Number 26680-10-4, and may be represented by the formula:

Poly(lactide-co-glycolide) or PLGA, includes poly(D,L-lactide-co-glycolide), also identified by CAS Number 26780-50-7, and may be represented by a formula:

Where x=the number of lactide repeating units and y=the number of glycolide repeating units. Thus, poly(D,L-lactide-co-glycolide) comprises one or more blocks of D,L-lactide repeat units and one or more blocks of glycolide repeat units, where the size and number of the respective blocks may vary.

The molar percent of each monomer (repeat unit) in a poly(lactide-co-glycolide) (PLGA) copolymer may be 0-100%, 15-85%, about 25-75%, or about 35-65%. In some embodiments, the D,L-lactide to glycolide ratio may be about 50:50 or about 75:25.

The PLA and/or PLGA polymer included in the polymer matrix may comprise ester or free carboxylic acid end groups.

PLA and PLGA polymers are available commercially from Evonik Industries AG, Germany, under the RESOMER® product line. Different RESOMER® polymers and combinations thereof may result in different release rates of a drug.

RESOMER® R203H is a poly(D,L-lactide) having an acid end group and an inherent viscosity of 0.25-0.35 dl/g, as measured for a 0.1% solution in chloroform at 25° C.

RESOMER® R203S is a poly(D,L-lactide) having an ester end group and an inherent viscosity of 0.25-0.35 dl/g, as measured for a 0.1% solution in chloroform at 25° C.

RESOMER® R202H is a poly(D,L-lactide) having an acid end group and an inherent viscosity of 0.16-0.24 dl/g, as measured for a 0.1% solution in chloroform at 25° C.

RESOMER® R202S is a poly(D,L-lactide) having an ester end group and an inherent viscosity of 0.16-0.24 dl/g, as measured for a 0.1% solution in chloroform at 25° C.

RESOMER® RG502 is a poly(D,L-lactide-co-glycolide) having an ester end group and an inherent viscosity of 0.16-0.24 dl/g (as measured for a 0.1% solution in chloroform at 25° C.), and a D,L-lactide:glycolide ratio of about 50:50.

RESOMER® RG502H is a poly(D,L-lactide-co-glycolide) having an acid end group and an inherent viscosity of 0.16-0.24 dl/g (as measured for a 0.1% solution in chloroform at 25° C.), and a D,L-lactide:glycolide ratio of about 50:50.

RESOMER® RG753S is a poly(D,L-lactide-co-glycolide) having an ester end group and an inherent viscosity of 0.32-0.44 dl/g (as measured for a 0.1% solution in chloroform at 25° C.), and a D,L-lactide:glycolide ratio of about 75:25.

RESOMER® RG752S is a poly(D,L-lactide-co-glycolide) having an ester end group and an inherent viscosity of 0.16-0.24 dl/g (as measured for a 0.1% solution in chloroform at 25° C.), and a D,L-lactide:glycolide ratio of about 75:25.

RESOMER® RG752H is a poly(D,L-lactide-co-glycolide) having an acid end group and an inherent viscosity of 0.14-0.22 dl/g (as measured for a 0.1% solution in chloroform at 25° C.), and a D,L-lactide:glycolide ratio of about 75:25.

As described above, a drug delivery system according to the present disclosure comprises a plurality of microspheres and an ophthalmically acceptable carrier. Ophthalmically acceptable carriers are carriers (e.g., liquids, oils, or gels) that are biocompatible with the eye, causing little or no injury to the eye. Two or more such carriers may be included in the drug delivery system. The microspheres may be suspended in the carrier. Accordingly, the drug delivery system can be in the form of a gel or suspension.

Examples of ophthalmically acceptable carriers include, but may not be limited to, sterile water; aqueous solutions comprising one or more buffering agents and having a pH of about 4 to about 8, or about 7.0 to about 7.8); and aqueous solutions (or gels) comprising hyaluronic acid (or an alkali or alkaline earth metal salt of hyaluronic acid such as sodium hyaluronate), hydroxyethyl cellulose (HEC), carboxymethylcellulose (CMC), hydrocypropylmethyl cellulose (HPMC), polyvinylproline (PVP), or a pluronic polymer.

These and additional aspects and embodiments of the invention can be further understood by reference to the following description, drawings, and examples.

BRIEF DESCRIPTION OF THE DRAWINGS

FIG. 7 shows the side view of two monkey eyes. The injection eye (left) shows that microspheres according to Example 6 fit into anterior chamber angle with minimal contact with the corneal endothelium; the control eye (right) indicates the empty space.

DEFINITIONS

For the purposes of this description, we use the following terms as defined in this section, unless the context of the word indicates a different meaning.

The term "biocompatible" means compatible with living tissue or a living system. Biocompatible implants produce few or no toxic effects, are not injurious, or physiologically reactive and do not cause an immunological reaction.

A "patient" refers to a human or non-human mammal, such as a primate, monkey, horse, dog, rabbit, rat, mouse, guinea pig, or pig, in need of treatment of a specified ocular condition.

As used herein, the term "ocular condition" refers to a disease or condition of one or more tissues, parts, or ocular regions of the eye that impairs the normal functioning of the eye. The anterior segment of the eye refers to the front third of the eyeball and includes structures located between the front surface of the cornea and the vitreous. The posterior segment of the eye refers to the rear two-thirds of the eyeball (behind the lens) and includes the vitreous, retina, optic disc, choroid, and pars plana.

The "eye" is the sense organ for sight, and includes the eyeball, or globe, the orbital sense organ that receives light and transmits visual information to the central nervous system. Broadly speaking the eye includes the eyeball and the tissues and fluids which constitute the eyeball, the periocular muscles (such as the oblique and rectus muscles) and the portion of the optic nerve which is within or adjacent to the eyeball.

The anterior chamber refers to the space inside the eye between the iris and the innermost corneal surface (corneal endothelium).

The anterior chamber angle refers to the junction of the front surface of the iris and back surface of the cornea.

The term "Intracameral" refers to the anterior chamber of the eye.

The term "associated with a biodegradable matrix" can mean mixed with or dispersed within, and/or surrounded by the matrix.

The term "biodegradable polymer" refers to a polymer or polymers which degrade in vivo, and wherein erosion of the polymer or polymers over time occurs concurrent with or subsequent to release of the therapeutic agent. The terms "biodegradable" and "bioerodible" are equivalent and are used interchangeably herein. A biodegradable polymer may be a homopolymer or a copolymer.

"Treating" and "treatment" include any beneficial or therapeutic effect in the eye or ocular tissue of a patient produced by administration of a drug delivery system as described herein, which effect can be a reduction of one or more signs and/or symptoms of the ocular condition or an improvement in the well being, visual performance and/or optical quality of the eye(s) in the individual. A reduction of one or more symptoms may include, but is not limited to, a reduction in ocular pain, inflammation, intraocular pressure, or discomfort. The sign(s) and symptom(s) positively affected by the treatment, will depend on the particular condition.

A "therapeutic agent," "active agent," "therapeutically effective agent," and "a therapeutic agent effective for the treatment of an ocular condition" refer to a pharmaceutically active agent (the drug substance) that relieves, reduces, or resolves at least one sign or symptom of the ocular condition.

The term "therapeutically effective amount" as used herein, refers to the level or amount of therapeutic agent needed to treat an ocular condition without causing significant negative or adverse side effects to the eye or a region of the eye or body part to which the agent is administered.

As used herein, an "ocular region" and "ocular region of the eye" refers generally to any area of the eyeball, including the anterior and posterior segment of the eye, and which generally includes, but is not limited to, any functional (e.g., for vision) or structural tissues found in the eyeball, or tissues or cellular layers that partly or completely line the interior or exterior of the eyeball. Specific examples of an ocular region of the eye include the anterior chamber, the posterior chamber, the vitreous body, the choroid, the supra-choroidal space, the conjunctiva, the subconjunctival space, the subTenon space, the episcleral space, the intracorneal space, the epicorneal space, the sclera, the pars plana, surgically-induced avascular regions, the macula, the retina, the iris, and the ciliary body (the circumferential tissue inside the eye composed of the ciliary muscle involved in lens accommodation, and ciliary processes that produce aqueous humor).

As used herein, an "ocular condition" is a disease, ailment or other medical condition of the eye which affects or involves the eye or one of the parts or ocular regions of the eye. Broadly speaking the eye includes the eyeball and the tissues and fluids which constitute the eyeball, the periocular muscles (such as the oblique and rectus muscles) and the portion of the optic nerve which is within or adjacent to the eyeball.

"Cumulative release profile" means the cumulative total percent of an active agent released from an implant into an ocular region or site in vivo over time or into a specific release medium in vitro over time.

DESCRIPTION

The present invention provides for a microsphere-containing drug delivery system, configured for injection into the anterior chamber (intracameral space) of an eye in a human or non-human mammal, that can provide for the sustained (>7 day) release of a therapeutic agent directly into the anterior chamber of the eye without causing significant swelling, inflammation, or hyperemia of the eye.

The basis for the invention is the discovery that microspheres greater than 40 µm in diameter and less than 200 µm in diameter are optimally suited for administration to the anterior chamber of the eye inasmuch as they are large enough to prevent rapid clearance through the trabecular meshwork but small enough to fit well within the anterior chamber angle of the anterior chamber without causing excessive eye redness. Comfortable retention in the anterior chamber enables the microspheres to provide for the sustained release of a therapeutic agent over a longer period of time with better patient tolerance as compared to smaller particles that are cleared more rapidly. Microspheres larger than 200 µm may be more difficult to inject with smaller gauge needles preferred for anterior chamber injection and may contact the corneal endothelium due to their larger size, causing undesirable effects.

Controlled and sustained administration of a therapeutic agent through the intracameral administration of microspheres according to the present disclosure may be effective for treating an undesirable ocular condition and thereby for improving the vision, function, and/or general well-being of an eye. Microspheres according to the present invention are particularly well suited for use in the treatment of glaucoma, since microspheres may provide continuous release of therapeutically effective amounts of anti-glaucoma drugs (such as prostamides) into the anterior chamber for extended periods lasting between 1 to 12 months. The microspheres comprise or consist of a therapeutic agent (or combination of therapeutic agents) and a biodegradable polymer matrix formulated to release the therapeutic agent(s) into the eye over an extended period of time. The therapeutic agent can be one that is effective for the treatment of a specific ocular condition and the extended period of time may be 1 month, 2 months, 3 months, or 6 months.

In some embodiments, the microspheres provide a therapeutically effective dosage of the agent(s) to a region of the eye (such as the anterior chamber) to treat or prevent one or more undesirable ocular conditions. Thus, with a single administration, a therapeutic agent is made available at the site where it is needed and is maintained for an extended period of time, rather than subjecting the patient to repeated injections or repeated administration of topical drops.

The microspheres of the present invention are preferably greater than 40 μm in diameter and less than 200 μm in diameter. In one embodiment the microspheres are greater than 40 μm and less than 150 μm in diameter. In another embodiment the microspheres are greater than about 106 μm and less than about 180 μm in diameter. As compared to smaller particles, microspheres of these sizes are ideally suited for administration to the anterior chamber of the eye because they are less likely to be rapidly eliminated through the trabecular meshwork and are also less prone to phagocytosis that can lead to undesirable inflammation and hyperemia in the eye. Maintaining the diameters below the indicated limits ensures the microspheres remain easily injectable through small gauge needles and enables the microspheres to settle into the anterior chamber angle of the eye without obscuring vision.

The biodegradable polymer matrix is designed to degrade at a rate effective to sustain release of an amount of the therapeutic agent for a time greater than about one week. For example, the biodegradable polymer matrix may provide continuous release of the therapeutic agent for about one month (30 days), two months, three months, or 6 months or more from the time the microspheres are placed in the anterior chamber of the eye.

The biodegradable polymer matrix may comprise one or more biodegradable polymers. For example the matrix may consist of first and second polymers that differ one from the other with regard to their end groups, inherent viscosity, and/or repeating units. In other embodiments, the microspheres may comprise first, second, and third biodegradable polymers. One or more of the biodegradable polymers may have terminal acid groups. For example, the microspheres may comprise a first biodegradable polymer having an ester end group and a different second biodegradable polymer having an acid end group. Useful biodegradable polymers which may be used independently or in combination include poly(D,L-lactide) polymers and poly(D,L-lactide-co-glycolide) copolymers. In addition, the microspheres may further comprise a polyethylene glycol (PEG). Useful polyethylene glycols include PEG 3350, PEG 4400, and PEG 8000.

The microspheres may be monolithic, i.e. having the active agent or agents homogenously distributed throughout the polymeric matrix, or encapsulated, where a reservoir of active agent is encapsulated by the polymeric matrix. In addition, the therapeutic agent may be distributed in a non-homogenous pattern in the matrix. For example, the microspheres may include a portion that has a greater concentration of the therapeutic agent relative to a second portion of the microspheres.

In the treatment of an ocular condition, the dosage of therapeutic agent used will depend on the condition being treated and the activity of the therapeutic agent. In the case of microspheres, if desired, doses up to a few milligrams of drug can be administrated via 20 microliter (μL) injections. Microspheres allow for easy dose adjustment. The volume of microspheres injected may vary from 5 μL to 200 μL. Typical volumes may be from about 10 μL to about 50 μL, and a volume of about 10 μL or 20 μL is suitable. Most often, the amount of microspheres delivered into the eye to treat an ocular condition will be about 0.1 mg to about 10 mg of microspheres per injection. For example, a single intracameral injection may contain about 0.5 mg or about 1 mg, or from about 0.5 mg to about 5 mg of microspheres, including the incorporated therapeutic component. For non-human patients, the total weight of the microsphere(s) may be adjusted larger or smaller, depending on the size of the mammal being treated, the pharmacological properties of the therapeutic agent, and the nature of the ocular condition. In preparation for injection, microspheres can be suspended in a suitable vehicle (i.e., an ophthalmically acceptable carrier) at any useful concentration. Suitable vehicles include aqueous liquids and hyaluronate gels. The concentration of hyaluronic acid or hyaluronate (for example, sodium hyaluronate) in a gel can vary between 0.1% and 5% w/v, for example. For example, a suitable vehicle for storing and injecting microspheres is an aqueous 2.5% w/v sodium hyaluronate gel. A suitable concentration of microspheres in a vehicle may vary depending on the desired dose of therapeutic agent, but can be, for example, about 5% (w/w) microspheres, or about 0.5 mg microspheres in 10 μL of vehicle.

The amount of therapeutic agent loaded into the microspheres will vary widely depending on the effective dosage required and the desired rate of release from the microspheres. Usually the therapeutic agent will be between about 2 and 30% by weight of the microsphere. In some instances the therapeutic agent constitutes at least about 5, more usually at least about 10 weight percent of the microsphere, or is about 25% weight percent of the microspheres. In some embodiments the microspheres comprise between about 5 and about 50% by weight therapeutic agent, or more specifically between about 5 and 30% by weight therapeutic agent.

The dosage of the therapeutic component in the microsphere is generally in the range from about 0.001 mg to about 10 mg per eye per intracameral dose, but also can vary from this depending upon the activity of the agent and its solubility.

The microspheres may be inserted into the anterior chamber of an eye by a variety of methods. A preferred means of administration is by intracameral injection using a syringe or like device equipped with a needle or cannula. A syringe apparatus including an appropriately sized needle, for example, a 22 gauge, 25 gauge, 27 gauge, 28 gauge, or a 30 gauge needle, can be effectively used to inject the composition into the anterior chamber of an eye of a patient.

In one embodiment the microspheres comprise one and no more than one therapeutic (pharmaceutically active) agent. For example, the microspheres may comprise a prostamide as the only therapeutic agent.

In other embodiments the microspheres comprise two or more therapeutic agents.

Alternatively, a single injection of microspheres may include two or more microsphere batches each containing a different therapeutic component or components. In addition, for dual therapy approaches to treating an ocular condition, the method may include one or more additional steps of administering additional therapeutic agents to the eye, such as by topically administering compositions to the eye, in addition to the anterior chamber administration of the microspheres.

Electrolytes such as sodium chloride and potassium chloride may also be included in the microspheres. Alternatively, or in addition, a polyethylene glycol such as PEG 3350, 4400, or 8000, may be included in the microsphere formulation to improve the properties of the microspheres.

Various techniques may be employed to produce the microspheres described herein. Useful techniques may include spray drying, microfluidics, and emulsion methods, including oil in water and oil in oil emulsion methods. Emulsion methods for preparing biodegradable microspheres comprising a prostamide, such as bimatoprost, and a biodegradable polymer matrix are described in, for example, U.S. Pat. No. 7,993,634 and in US Application Publication 2006/0246145. In the present invention, sieves are used in conjunction with the emulsion process to specifically select for microspheres having the required maximum and minimum particle sizes. In general, the method uses a series of two sieves having different relative mesh sizes to obtain a microsphere population meeting the desired maximum and minimum size parameters. The initial microsphere population (generated, for example, by an emulsion method, such as that described above) is filtered through a first sieve to remove particles larger than the mesh size of the first sieve. The microspheres that pass through the first sieve are then filtered through a second sieve to trap and collect microspheres larger than the mesh size of the second sieve. Thus, in this process, the mesh size of the first sieve is selected so as to be larger than the mesh size of the second sieve. With this two-step sieving process one obtains a population of microspheres with particle sizes smaller than the mesh size of the first sieve and larger than the mesh size of the second sieve. By selecting the appropriate combination sieves, it is possible to generate a population of microspheres meeting the desired maximum and minimum cutoffs suitable for administration into the anterior chamber. Many combinations of sieves can be used to generate a population of microspheres having particles sizes smaller than 200 μm and larger than about 40 μm. In some forms of the invention it may be useful to ensure the particle sizes are smaller than 200 μm and larger than 40 μm. In a useful form of the method the mesh size of the first sieve is 180 μm and the mesh size of the second sieve is 106 μm, such that the microspheres obtained with the method have particles sizes greater than about 106 μm and smaller than about 180 μm. In another form, the mesh size of the first sieve is 106 μm and the mesh size of the second sieve is 40 μm. Other sieve combinations may be used to prepare a population of microspheres having the desired maximum and minimum particle sizes, within the limits described and recommended by the present disclosure. Microspheres obtained with the 106 μm and 180 μm sieve combination may be particularly useful for their drug load capacity, release kinetics, retention in the anterior chamber, and ease of injection.

Alternative methods for selecting for microspheres with desired maximum and minimum particle sizes include microfluidics, microsieves, sedimentation, and various methods of fractionation.

The present methods may also comprise a step of terminally sterilizing the microspheres. The method may comprise exposing the present microspheres to sterilizing amounts of gamma radiation, e-beam radiation, and/or other terminal sterilization products. In one embodiment, a method may comprise a step of exposing the present microparticles to gamma radiation at a dose of about 25 kGy.

In accordance with the present disclosure, the present invention includes, but is not limited to, the following embodiments (1-32):

1. A drug delivery system effective for the treatment of an ocular condition, the system comprising a plurality of biodegradable microspheres and an ophthalmically acceptable carrier, the biodegradable microspheres having diameters no less than 40 μm and no greater than 200 μm and comprising a biodegradable polymer matrix and a therapeutic agent effective for the treatment of the ocular condition, wherein the drug delivery system comprises no microspheres smaller than 40 μm and no microspheres larger than 200 μm, and wherein the drug delivery system releases a therapeutically effective amount of the therapeutic agent for at least one week after the system is placed in an eye of a mammal 2. A drug delivery system according to embodiment 1, wherein the microspheres present in the drug delivery system are produced by an emulsion process.

3. A drug delivery system according to embodiment 2, wherein the plurality of biodegradable microspheres present in the drug delivery system have diameters no less than about 106 μm and no greater than about 180 μm, such that the drug delivery system comprises no microspheres smaller than about 106 μm and no microspheres larger than about 180 μm.

4. A drug delivery system according to embodiment 3, wherein the mean diameter of the microspheres present in the drug delivery system is between 100 μm and 150 μm.

5. A drug delivery system according to embodiment 4, wherein the mean diameter of the microspheres present in the drug delivery system is between 110 μm and 150 μm.

6. A drug delivery system according to embodiment 4 or 5, wherein the ocular condition is glaucoma, elevated intraocular pressure, neovascularization, or inflammation.

7. A drug delivery system according to embodiment 6, wherein the therapeutic agent is a prostamide, prostaglandin, protein, DARPin, anticalin, steroidal anti-inflammatory agent, non-steroidal anti-inflammatory agent, alpha 2 adrenergic receptor agonist, or tyrosine kinase inhibitor.

8. A drug delivery system according to embodiment 7, wherein the ocular condition is glaucoma, elevated intraocular pressure, or inflammation and the therapeutic agent is bimatoprost, a steroidal anti-inflammatory agent, or a non-steroidal anti-inflammatory agent.

9. A drug delivery system according to embodiment 8, wherein the ocular condition is glaucoma or elevated intraocular pressure and the therapeutic agent is bimatoprost and the drug delivery system comprises no therapeutic agent other than bimatoprost.

10. A drug delivery system according to any of embodiments 6-9, wherein the ophthalmically acceptable carrier is an aqueous liquid or gel comprising a hyaluronic acid, a sodium hyaluronate, a hydroxyethyl cellulose (HEC), a carboxymethylcellulose (CMC), a hydroxypropylmethyl cellulose (HPMC), a polyvinylproline (PVP), or a pluronic polymer.

11. A drug delivery system according to embodiment 10, wherein the ophthalmically acceptable carrier is an aqueous gel comprising 2.5% w/v sodium hyaluronate.

12. A drug delivery system according to embodiment 10 or 11, wherein the biodegradable polymer matrix comprises a poly(D,L-lactide), a poly(D,L-lactide-co-glycolide), or a mixture thereof 13. A drug delivery system according to embodiment 12, wherein the poly(D,L-lactide) and/or poly(D,L-lactide-co-glycolide) are independently selected from the group consisting of RESOMER® R203S, R203H, RG752H, RG755, RG502H, RG752S, R202H, R202S, and RG753S

14. A drug delivery system according to embodiment 13, wherein the biodegradable polymer matrix further comprises a polyethylene glycol (PEG).

15. A drug delivery system according to embodiment 14, wherein the PEG is PEG 3350, PEG 4400, or PEG 8000.

16. A drug delivery system according to any of embodiments 13-15, wherein the therapeutic agent is bimatoprost and the ocular condition is glaucoma.

17. A drug delivery system according to embodiment 16, wherein the microspheres present in the drug delivery system comprise any of the formulations defined by Table 1.

18. An apparatus for injecting a drug delivery system into the eye of a mammal, said apparatus comprising a cannula, said cannula having a proximal end, a distal sharp end, and a lumen extending therethrough, the cannula further comprising a drug delivery system as defined by any of embodiments 1-17, wherein the drug delivery system is located within the lumen of the cannula.
19. A method for treating an ocular condition in an eye of a patient in need thereof, the method comprising placing a drug delivery system according to any of embodiments 1-17 in the anterior chamber of the patient's eye, thereby reducing at least one symptom of the ocular condition for at least one week.
20. A method according to embodiment 19, wherein the ocular condition in the eye is glaucoma, elevated intraocular pressure, or an inflammation in the eye, and the drug delivery system is effective for reducing at least one symptom of the ocular condition for two weeks or more after placement in the anterior chamber of the patient's eye(s).
21. A method according to embodiment 20, wherein the microspheres in the drug delivery system fit into the angle between the cornea and iris of the eye (the anterior chamber angle) and are retained in the anterior chamber of the eye for at least 48 hours after administration.
22. A method according to embodiment 21, wherein administration of the microspheres does not cause hyperemia or inflammation in the eye or augment existing hyperemia or inflammation in the eye.
23. A method according to embodiment 22, wherein the patient is a human or non-human mammal
24. A method for making a population of biodegradable microspheres, the process comprising
    a) dissolving a biodegradable polymer or combination of two or more biodegradable polymers and a quantity of therapeutic agent in an organic solvent or mixture of solvents to form a solution;
    b) adding a saturating or non-saturating quantity of therapeutic agent to an aqueous solution of polyvinyl alcohol to form a second solution;
    c) adding the first solution to the second solution dropwise under constant stirring to form an emulsion;
    d) evaporating the solvent(s) under constant stirring to form a suspension;
    e) filtering the suspension through first and second sieves, wherein the mesh size of the first sieve is larger than the mesh size of the second sieve, thereby collecting particles with diameters less than the mesh size of the first sieve and greater than the mesh size of the second sieve;
    f) centrifuging the collected particles to obtain a pellet;
    g) lyophilizing the pellet, thereby obtaining a microsphere population.
25. The method of embodiment 24, wherein the first and second sieves have mesh sizes of 180 µm and 106 µm, respectively.
26. The method of embodiment 25, wherein the mean diameter of the microsphere population obtained at Step g is between 100 µm and 150 µm.
27. The method of embodiment 26, wherein the mean diameter of the microsphere population obtained at Step g is between 110 µm and 150 µm.
28. A method of making a population of biodegradable microspheres according to any of embodiments 24-27, further comprising washing the pellet obtained at step f with water before lyophilizing the pellet.
29. A method of making a population of biodegradable microspheres according to any of embodiments 24-27, wherein the therapeutic agent is effective for reducing intraocular pressure (IOP), reducing inflammation of the eye, or treating glaucoma in the eye.
30. The method of embodiment 29, wherein the therapeutic agent is a prostamide or a steroidal anti-inflammatory agent.
31. The method of embodiment 30, wherein the therapeutic agent is bimatoprost or the compound having the formula 32. A population of microspheres produced by the method of any of embodiments 24-31.

EXAMPLES

Example 1

Manufacture and Testing of Biodegradable Microspheres Containing Bimatoprost

A drug/polymer solution was obtained by dissolving bimatoprost (100 mg) and the PLGA polymer RESOMER® RG752S (300 mg) in an organic solvent mixture of ethyl acetate (2.4 mL) and methanol (0.2 mL). This drug/polymer solution was then added dropwise to 40 mL of a 1% PVA and 0.1% bimatoprost aqueous solution while stirring moderately at 300 rpm. The resulting suspension was then stirred at room temperature in a fume hood for 3-4 hrs to let the organic solvents evaporate. After the drug loaded PLGA particles hardened, the suspension was filtered through 180 and 106 µm sieves.

Particles less than 180 µm and greater than 106 µm were collected. The collected suspension was centrifuged at 2000 rpm for 15 min to remove the supernatant, and the final white microspheres were obtained by lyophilization. Further characterization indicated the average size of the microspheres was 136 µm, and bimatoprost loading (% bimatoprost by weight of microspheres) was 11.1% w/w.

To prepare microspheres that further include a polyethylene glycol, a specified amount of the PEG is added to the organic solvent mixture along with the RESOMER® polymer(s) and bimatoprost to form the drug/polymer solution.

Examples of bimatoprost microsphere formulations prepared according to the method described above using various RESOMER® polymers and combinations of polymers are listed in Table 1. The values in parentheses indicate the weight to weight ratio of each constituent in the drug/polymer composition.

The release of bimatoprost from a microsphere preparation in vitro was measured by suspending about 15 mg of microspheres in 10 ml of phosphate-buffered saline (pH 7.4)

solution (release medium). The release medium was incubated at 37° C. in a water bath (Model 25 Reciprocal Shaking Water Bath, Precision Scientific, Ontario N.Y.) with a shaking speed of 40 rpm. At predetermined time intervals, the samples were centrifuged and the supernatant was completely removed and kept for HPLC analysis. The microspheres were re-suspended in fresh release medium after each time point. The studies were performed in triplicate for each batch of formulation and the results were expressed as the mean (n=3).

Figure 1A:
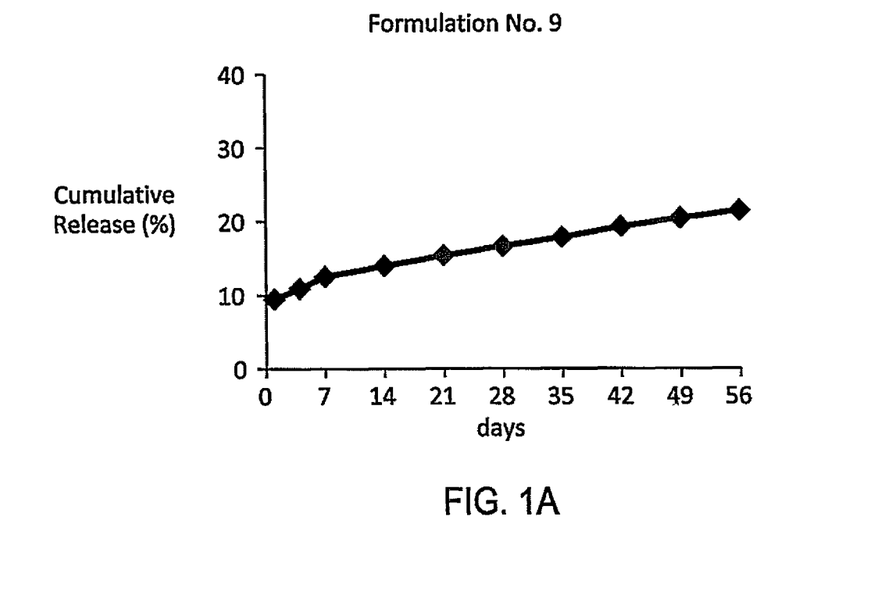
FIGS. 1A and B show the in vitro cumulative percentage release (cumulative release profile) of bimatoprost into phosphate buffered saline solution at 37° C. for selected microsphere formulations from Example 1.
Figure 1B:
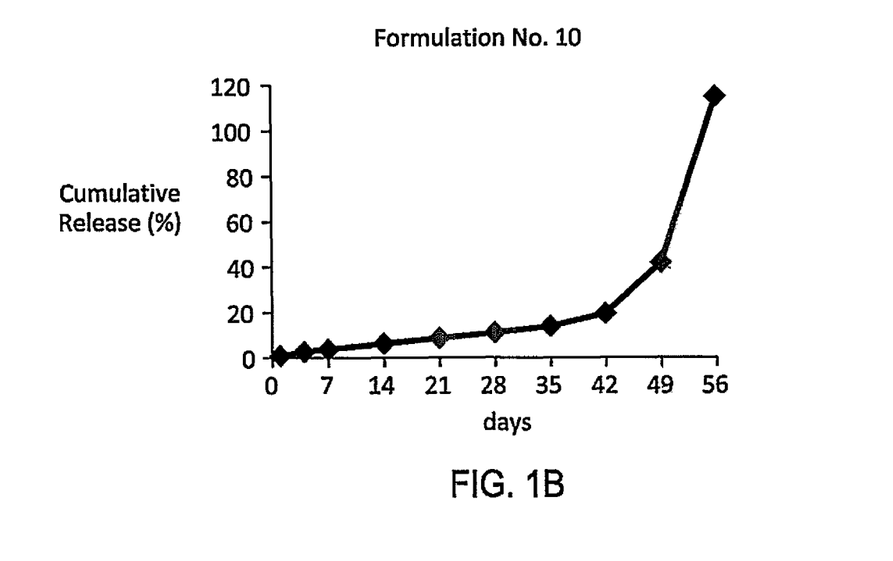

The rate of bimatoprost release from Formulation Nos. 9 and 10 (plotted as the cumulative amount of bimatoprost released as a percent of the total amount initially present in the sample, i.e., as the percent cumulative release) over time are shown in FIGS. 1A and B, respectively.

TABLE 1

Bimatoprost microsphere formulations prepared according to Example 1

| Formulation No. | Polymer(s) | Microsphere yield % | Mean particle size (μm) | Bimatoprost % (w/w) |
|---|---|---|---|---|
| 1 | RG752H | 18.3 | 118 | 3.5 |
| 2 | R203S/RG752S/R202H/PEG3350 (9:4:2:1) | 7.1 | 117 | 15.2 |
| 3 | R203H:RG502H (3:1) | 27.9 | 137 | 14.9 |
| 4 | RG755:RG502H (3:1) | 5.0 | 109 | 15.6 |
| 5 | R203H:PEG3350 (9:1) | 7.1 | 126 | 19.6 |
| 6 | R203H/PEG3350 (14:1) | 10.4 | 141 | 6.1 |
| 7 | R203H/RG502 (6.5:1) | 10.8 | 123 | 10.5 |
| 8 | R203S/PEG3350 (14:1) | 6.6 | 138 | 12.1 |
| 9 | R202S/PEG3350 (14:1) | 13.7 | 142 | 7.2 |
| 10 | RG752S | 9.6 | 136 | 11.1 |
| 11 | RG753S/PEG3350 (14:1) | 19.9 | 137 | 9.4 |
| 12 | R203S/PEG4400 (14:1) | 4.6 | 131 | 9.2 |
| 13 | R203S/PEG8000 (14:1) | 6.3 | 116 | 11.4 |
| 14 | RG753S/PEG4400 (14:1) | 17.1 | 127 | 8.3 |
| 15 | RG753S/PEG8000 (14:1) | 15.4 | 129 | 8.0 |

TABLE 2

Formulation No. 10 bimatoprost-containing microspheres for in vivo testing in dogs
Formulation No. 10

| | |
|---|---|
| Bimatoprost wt % | 7.3 |
| Average particle size (μm) | 108.0 |
| % Microspheres/HA gel | 5% |
| Intracameral dose | 20 μl |
| Microspheres mg/eye | 1 mg |
| Bimatoprost (μg/eye) | 73 μg |
| Daily dose | 290 ng/day |
| Number of Animals | 3 |

Example 2

Bimatoprost Microsphere Study in Dogs

Figure 2:
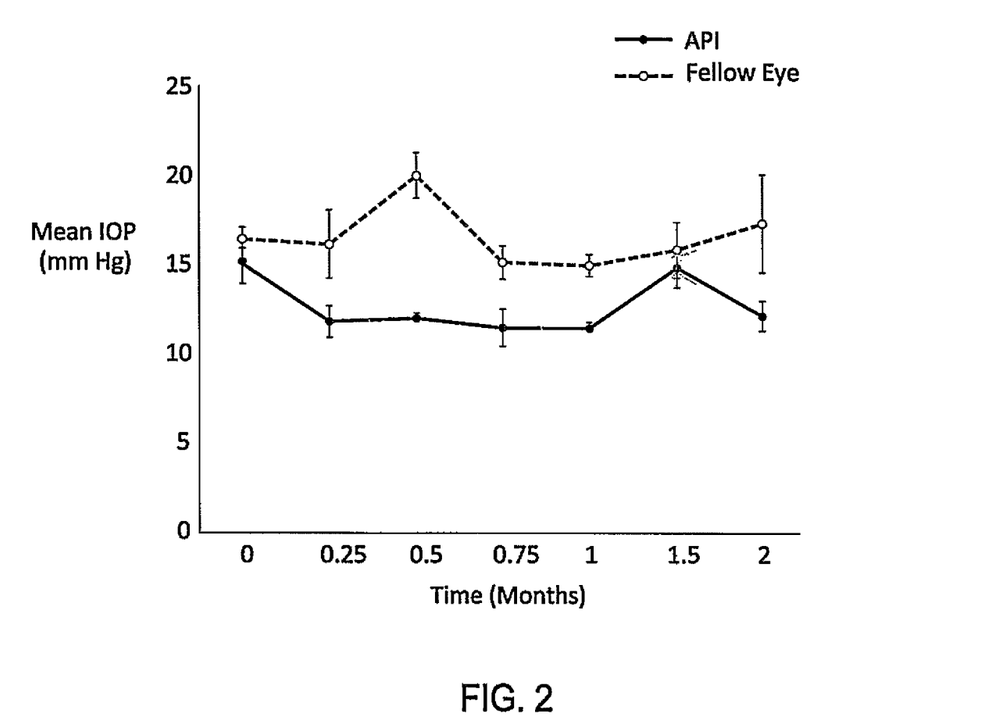
FIG. 2 shows the reduction in intraocular pressure (IOP) in dogs dosed with bimatoprost-loaded microspheres (API, Formulation No. 10), as described in Example 2.

Formulation No. 10 was selected and prepared for dog studies (Table 2). The injectable formulations consisted of 5% microspheres in a hyaluronic acid (HA) gel (aqueous 2.5% w/v). For each dog, a 20 μl volume of the suspension was injected into the intracameral chamber of the left eye (API), while the right eye (fellow eye) was left untreated as a control. The injected viscous gel formulation contained about 1 mg microspheres, in which about 73 μg bimatoprost drug was encapsulated. Based on the in vitro release profile, it is estimated that the microspheres may have provided about 290 ng of bimatoprost to the eye per day. The intraocular pressure (IOP) was measured weekly till the end of efficacy period. Other observations made included specular microscopy and slit lamp exams with gonioscopy. Based on the two month observation, the microspheres were well tolerated. On average, over the two month period, the IOP for untreated eyes was about 16 mm Hg, while the IOP in treated eyes remained lower at about 11 mm Hg, a difference of about 30%. (FIG. 2)

Example 3

Microsphere Placement in the Anterior Chamber Angle of the Eye

Figure 3:
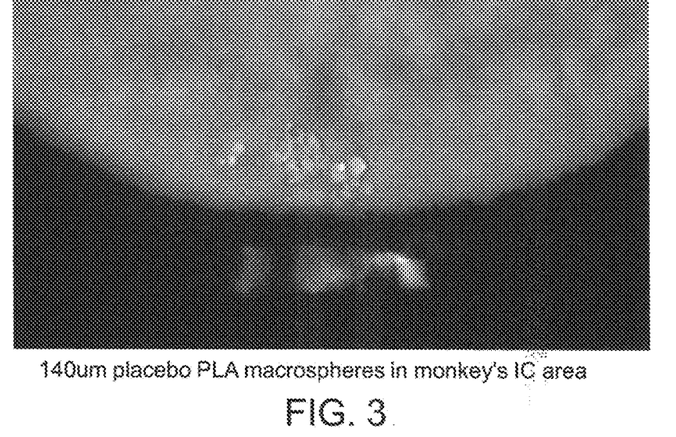
FIG. 3 shows a photo of placebo PLA microspheres in the intracameral (IC) space of a monkey eye, according to Example 3. The mean particle size of the microspheres was 140 μm

Placebo microspheres (30 μL, 1.5 mg) having a mean diameter of 140 μm were injected into the anterior chamber of an eye in a monkey. The photo in FIG. 3, taken three days after injection, shows the microspheres fit nicely into the angle between the cornea and the iris (the anterior chamber angle). No adverse effects have been observed 4 months after injection.

Example 4

Injection of Microspheres into the Anterior Chamber of Dogs

Figure 4:
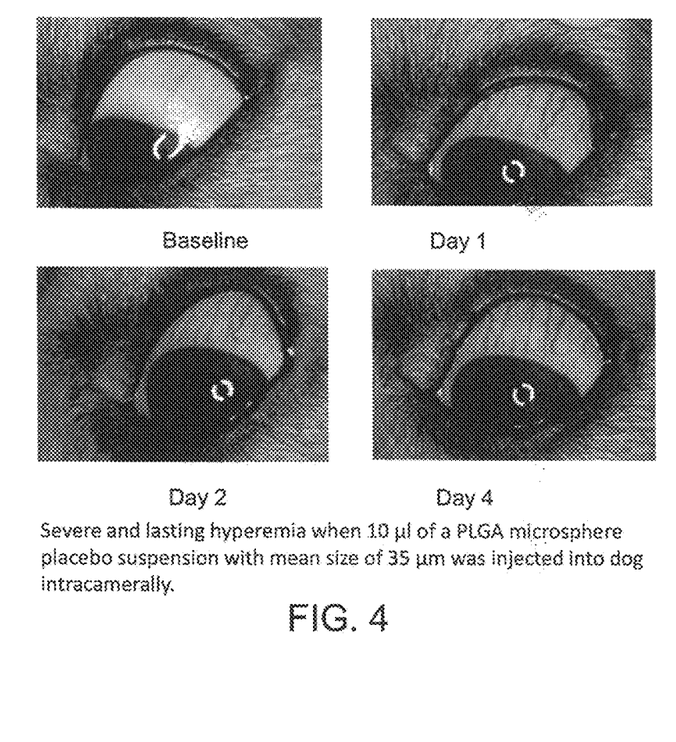
FIG. 4 shows severe and lasting hyperemia in a dog eye one, two, and four days after injecting 10 μL of a PLGA microsphere placebo suspension with a mean particle size of 35 μm into the intracameral space of the eye, as described in Example 4.

Severe hyperemia has been observed when microspheres with a mean size of about 35 μm were injected into the anterior chamber of a dog (intracameral administration; FIG. 4). An additional drawback is that these microspheres are not retained in the anterior chamber after intracameral administration. The microspheres were found to clear from the chamber through the trabecular meshwork. The trabecular meshwork is a 3 dimensional sponge-like structure with mesh sizes ranging from 20-30 μm. One day after injection no microspheres were visible in the aqueous humor by visual and slit lamp inspection.

Example 5

Injection of Microspheres into the Anterior Chamber of Dogs

Figure 5:
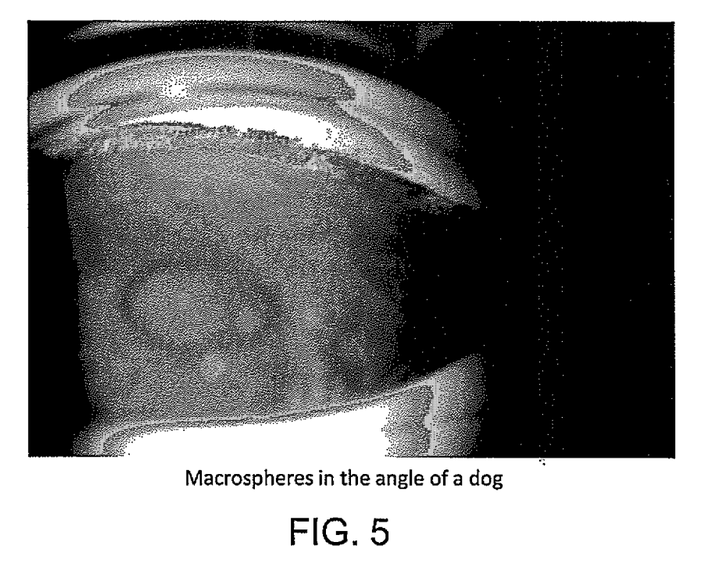
FIG. 5 shows placebo microspheres (bimatoprost-free Formulation No. 10) settled into the anterior chamber angle of a dog eye at week 1 after injection, as described in Example 5. In this case, about 1 mg of placebo microspheres having a mean particle size of 136 μm was injected through a 25 G UTW needle. No hyperemia or inflammation was observed.

FIG. 5 shows placebo microspheres (Formulation No. 10 without drug) settled into the anterior chamber angle of a dog at one week after injection. In this case, placebo microspheres (about 1 mg) having a mean diameter of 136 µm were injected through a 25 gauge UTW needle. In this case no hyperemia or inflammation was observed after one month.

Example 6

Injection of Latanoprost-Containing Microspheres into the Anterior Chamber of Dogs and Monkeys Several latanoprost-containing microsphere formulations were manufactured and tested in the dog anterior chamber. Specifically, two latanoprost-containing microsphere formulations, Nos. 16 and 17, were evaluated. The injectable formulations consisted of 5% (w/w) microspheres in an aqueous 2.5% (w/v) hyaluronic acid gel. A total of 10 µL of the formulation was injected into the anterior chamber of one eye in each dog. The mean particle size of the No. 16 and 17 formulations were 141 µm and 159.8 µm, respectively. A total dose of 125 µg of latanoprost was given in a total microsphere dose of 500 µg (25% drug load). Two dogs per formulation were tested. The dogs were followed for at least 2 months with intraocular pressure (IOP), gross ocular observation (GOO), and slit lamp. Both microsphere formulations were found to be well tolerated after two months in the eye. The corneas were clear and no inflammation was detected in any of the treated eyes.

Figure 6:
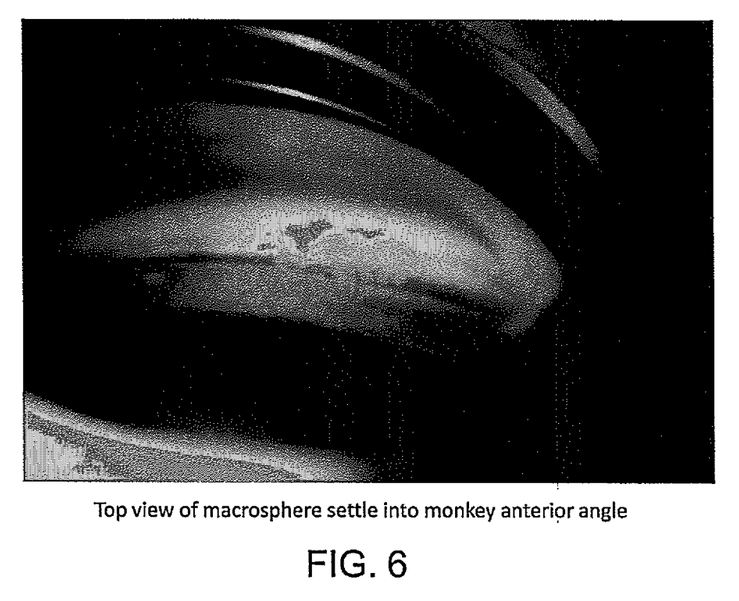
FIG. 6 shows the top view of microspheres from Example 6 settled into the anterior chamber angle of a monkey eye.
Figure 7:
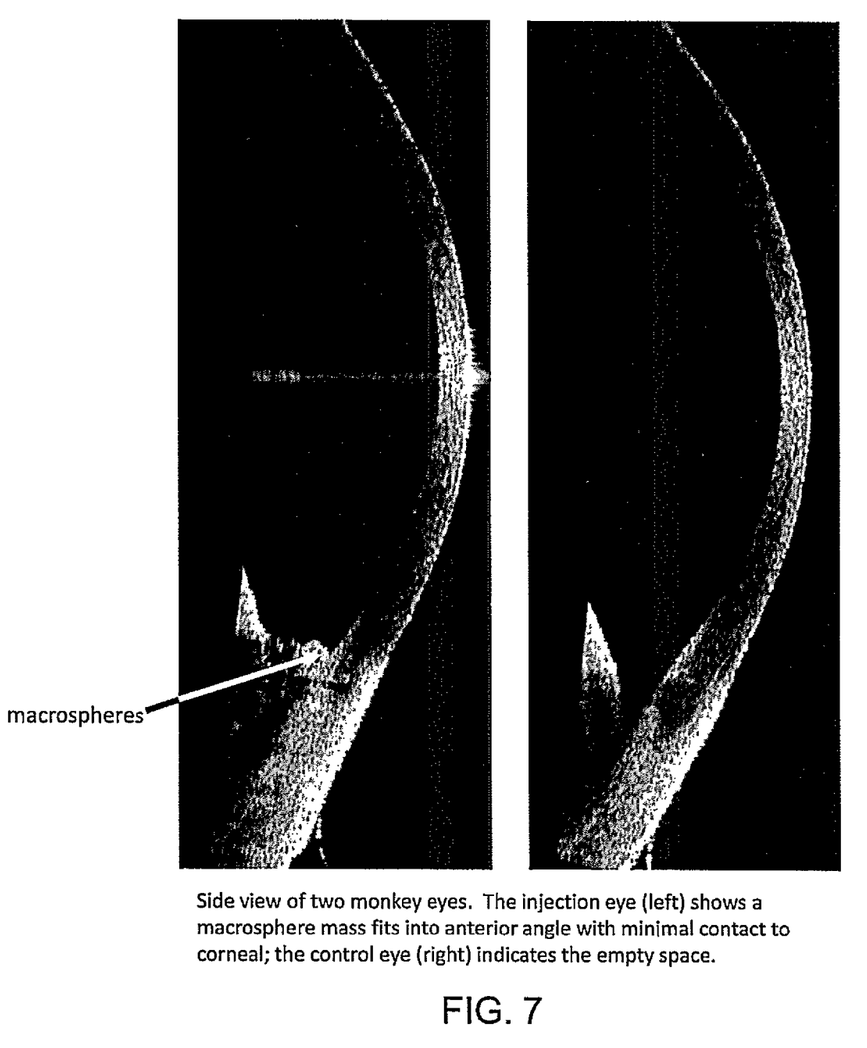

Formulation Nos. 16 and 17 were also dosed in monkeys, and their placement and distribution are illustrated in FIGS. 6 and 7. FIG. 6 shows that the microspheres were retained in the anterior chamber, and they were not cleared through the trabecular meshwork. FIG. 7 illustrates from a side view that the microspheres settled down in the anterior chamber angle of the eye.

What is claimed is:

1. A drug delivery system effective for the treatment of an ocular condition,
   the system comprising a plurality of biodegradable microspheres and an ophthalmically acceptable carrier;
   the biodegradable microspheres having diameters no less than about 130 microns and no greater than about 160 microns and comprising a biodegradable polymer matrix and a therapeutic agent effective for the treatment of the ocular condition; and
   wherein the drug delivery system releases a therapeutically effective amount of the therapeutic agent for at least one week after the system is placed in an eye of a patient.

2. The drug delivery system according to claim 1, wherein the microspheres present in the drug delivery system are produced by an emulsion process.

3. The drug delivery system according to claim 1, wherein the ocular condition is glaucoma, elevated intraocular pressure, neovascularization, or inflammation.

4. The drug delivery system according to claim 3, wherein the therapeutic agent is a prostamide, prostaglandin, steroidal anti-inflammatory agent, non-steroidal anti-inflammatory agent, alpha 2 adrenergic receptor agonist, or tyrosine kinase inhibitor.

5. The drug delivery system according to claim 4, wherein the ocular condition is glaucoma or an inflammation of the eye of the patient and the therapeutic agent is bimatoprost, a steroidal anti-inflammatory agent, or a non-steroidal anti-inflammatory agent.

6. The drug delivery system according to claim 5, wherein the ocular condition is glaucoma or elevated intraocular pressure and the therapeutic agent is bimatoprost and the drug delivery system comprises no therapeutic agent other than bimatoprost.

7. The drug delivery system according to claim 4, wherein the therapeutic agent is a compound having the formula:

8. The drug delivery system according to claim 1, wherein the ophthalmically acceptable carrier is an aqueous liquid or gel comprising a hyaluronic acid, a sodium hyaluronate, a hydroxyethyl cellulose (HEC), a carboxymethylcellulose (CMC), a hydroxypropylmethyl cellulose (HPMC), a polyvinylproline (PVP), or a pluronic polymer.

9. The drug delivery system according to claim 8, wherein the ophthalmically acceptable carrier is an aqueous gel comprising 2.5% w/v sodium hyaluronate.

10. The drug delivery system according to claim 8, wherein the biodegradable polymer matrix comprises a poly(D,L-lactide), a poly(D,L-lactide-co-glycolide), or a mixture thereof.

11. The drug delivery system according to claim 10, wherein each said poly(D,L-lactide) and poly(D,L-lactide-co-glycolide) is independently selected from the group consisting of R203S, R203H, RG752H, RG755, RG502, RG502H, RG752S, R202H, R202S, and RG753S.

12. The drug delivery system according to claim 11, wherein the biodegradable polymer matrix further comprises a polyethylene glycol (PEG).

13. The drug delivery system according to claim 12, wherein the PEG is PEG 3350, PEG 4400, or PEG 8000.

14. The drug delivery system according to claim 12, wherein the therapeutic agent is bimatoprost and the ocular condition is glaucoma.

15. The drug delivery system according to claim 1, wherein the plurality of microspheres have a polydispersity of not more than about 5, wherein the polydispersity is the microsphere particle size distribution measured by d90/d10,
   wherein d90 is the diameter below which 90% of the particles fall, and d10 is the diameter below which 10% of the particles fall.

16. The drug delivery system according to claim 1, wherein the microspheres are effectively retained in the anterior chamber of the eye of the patient without producing hyperemia.

17. The drug delivery system according to claim 1, wherein the patient is a human.

\* \* \* \* \*